US008404872B2

(12) United States Patent
Njardarson et al.

(10) Patent No.: US 8,404,872 B2
(45) Date of Patent: Mar. 26, 2013

(54) PRODUCTION OF 2,5-DIHYDROFURANS AND ANALOGOUS COMPOUNDS

(75) Inventors: Jon Njardarson, Ithaca, NY (US); Lindsay Batory, Ithaca, NY (US); Matthew Brichacek, Little Falls, MN (US); Renato Bauer, Pepperell, MA (US); Erik Rogers, Lake View, NY (US)

(73) Assignee: Cornell University, Ithaca, NY (US)

( * ) Notice: Subject to any disclaimer, the term of this patent is extended or adjusted under 35 U.S.C. 154(b) by 224 days.

(21) Appl. No.: 12/224,711

(22) PCT Filed: Mar. 12, 2007

(86) PCT No.: PCT/US2007/006216
§ 371 (c)(1),
(2), (4) Date: Dec. 12, 2008

(87) PCT Pub. No.: WO2007/108999
PCT Pub. Date: Sep. 27, 2007

(65) Prior Publication Data
US 2009/0131691 A1    May 21, 2009

Related U.S. Application Data

(60) Provisional application No. 60/783,063, filed on Mar. 17, 2006.

(51) Int. Cl.
C07D 307/28    (2006.01)
C07D 303/00    (2006.01)
C07D 333/02    (2006.01)
C07D 409/02    (2006.01)
C07D 207/18    (2006.01)
C07D 203/04    (2006.01)

(52) U.S. Cl. .......... 549/507; 549/29; 549/512; 549/513; 549/49; 548/565; 548/954

(58) Field of Classification Search .................. 549/512, 549/513, 507, 29, 1, 49; 548/565, 954
See application file for complete search history.

(56) References Cited

U.S. PATENT DOCUMENTS

| | | | |
|---|---|---|---|
| 3,812,158 A | 5/1974 | Besozzi et al. |
| 3,932,468 A | 1/1976 | Kurkov |
| 3,996,248 A | 12/1976 | Wall et al. |
| 5,034,545 A | 7/1991 | Fischer |
| 5,082,956 A | 1/1992 | Monnier et al. |
| 5,238,889 A | 8/1993 | Falling et al. |
| 5,315,019 A | 5/1994 | Phillips et al. |
| 5,391,771 A | 2/1995 | Weyer et al. |
| 5,466,832 A | 11/1995 | Tustin |
| 5,536,854 A | 7/1996 | Weyer et al. |
| 5,618,953 A | 4/1997 | Abe et al. |
| 5,663,382 A | 9/1997 | Takemoto et al. |
| 5,856,531 A | 1/1999 | Beavers |
| 5,872,266 A | 2/1999 | Nitobe et al. |
| 5,883,266 A | 3/1999 | Elliott et al. |
| 5,912,364 A | 6/1999 | Beavers |
| 5,990,324 A | 11/1999 | Takemoto et al. |
| 6,147,233 A | 11/2000 | Beavers |
| 6,239,295 B1 | 5/2001 | Iwasaki |
| 6,479,677 B1 | 11/2002 | Ahmed |
| 6,521,765 B1 | 2/2003 | Ignatchenko et al. |
| 6,673,946 B2 | 1/2004 | Manzer |
| 6,812,354 B2 | 11/2004 | Beavers et al. |
| 6,852,868 B2 | 2/2005 | Ahmed |
| 2003/0109724 A1 | 6/2003 | Manzer |
| 2004/0119052 A1 | 6/2004 | Beavers et al. |
| 2005/0176974 A1 | 8/2005 | Ahmed |

FOREIGN PATENT DOCUMENTS

| | | |
|---|---|---|
| CN | 1454894 | 11/2003 |
| EP | 0589314 | 9/1993 |
| EP | 0690053 | * 1/1996 |
| EP | 0691334 | 1/1996 |
| JP | 2000063372 | 2/2000 |
| WO | 99/35137 | 7/1999 |

OTHER PUBLICATIONS

Translation of Japanese equivalent of EP 0690053.*
Fischer et al, CAS Abstract, 1996.*
Batory, L.A., et al. J. Am. Chem. Soc. 2006, 128, 16054-16055.
Mel'nik, L.V., et al. Petroleum Chemistry, vol. 43, No. 3, 2003, 167-169.
Bobyleva, L.I., et al., Synthesis of 2,5-Dihydrofuran and Tetrahydrofuran from 1,3-Butadiene, Petroleum Chemistry, 2004, vol. 44, No. 3. pp. 188-192.

(Continued)

Primary Examiner — Taylor Victor Oh
(74) Attorney, Agent, or Firm — Hodgson Russ LLP

(57) ABSTRACT

Vinyl oxiranes are rearranged to 2,5-dihydrofuran using catalyst (III) or (IV). The 2,5-dihydrofuran can be reduced to tetrahydrofuran. 3,4-Epoxy-1-butene substrate is converted to 2,5-dihydrofuran which in turn is converted to tetrahydrofuran. Substrate for making 3-methyltetrahydrofuran is prepared from isoprene. Substrate for making 2-methyltetrahydrofuran is prepared from piperylene. Reactions analogous to that with vinyl oxiranes are carried out with vinyl thiiranes and vinyl aziridines.

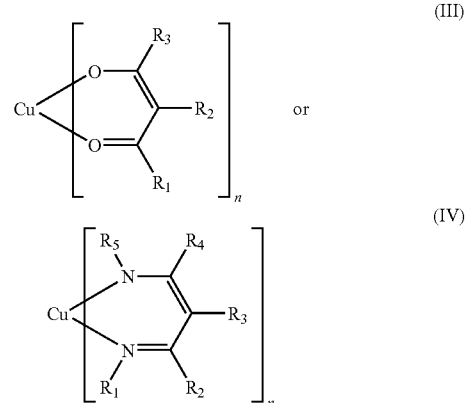

27 Claims, No Drawings

OTHER PUBLICATIONS

Remans, T.J., et al., Iodide Assisted Zeolite Catalysed 1,4-Addition of Water to Butadiene Monoxide, J. Catal., 1998, vol. 175, pp. 312-315.

Fasi, A., et al., Ring-opening reactions of ethyl- and vinyuloxirane on HZSM-5 and CuZSM-5 catalysts, Surf. Sci. Catal., 2000, vol. 130, pp. 839-844.

* cited by examiner

PRODUCTION OF 2,5-DIHYDROFURANS AND ANALOGOUS COMPOUNDS

CROSS-REFERENCE TO RELATED APPLICATIONS

This application claims the benefit of U.S. Provisional Application No. 60/783,063, filed Mar. 17, 2006, the whole of which is incorporated herein by reference.

TECHNICAL FIELD

This invention is directed to production of 2,5-dihydrofurans, and to production of analogous compounds.

BACKGROUND OF THE INVENTION 2,5-Dihydrofurans, 2,5-dihydrothiophenes, and 2,5-dihydro-1H-pyrroles (3-pyrrolines) are building blocks for the pharmaceutical and commodity chemical industry. 2,5-Dihydrofurans are reduced to tetrahydrofurans. 2,5-Dihydrothiophenes are reduced to tetrahydrothiophenes or oxidized to thiophenes. 2,5-Dihydro-1H-pyrroles are reduced to pyrrolidines. Tetrahydrofuran is a chemical of commerce and a common organic solvent. A number of substituted tetrahydrofuran derivatives are also produced in great quantities for use as solvents, polymer building blocks and for various other purposes. Tetrahydrofurans are also useful as starting materials for synthesis of polyether polyols. 3-Methyltetrahydrofuran is an important building block for production of elastomers and is used as a solvent when a higher boiling point than that of tetrahydrofuran is necessary. 2-Methyltetrahydrofuran is a replacement solvent for dichloromethane and is a superior solvent for performing Grignard reactions as well as a cleaner burning co-solvent for spark ignition motorfuel. Tetrahydrothiophenes are useful as antimycotic agents, and as odorants in natural gas. Tetrahydrothiophene is useful as an intermediate in the production of the solvent sulfolane (produced by oxidation of tetrahydrothiophene). Thiophene is a decomposition product of tetrahydrothiophene. Thiophenes are recurring building blocks in organic chemistry with applications in pharmaceuticals. 3-Alkyl and 3-arylthiophenes are important building blocks for conductive polymers. The pyrrolidine ring structures are found in many pharmaceutical drugs such as procyclidine, enalapril, clindamycin, hyoscyamine, fosinopril, altace, combivent and kytril. A pyrrolidine ring is the central structure of the amino acids proline and hydroxyproline. Pyrrolidines are also useful to treat hormone refractory prostate cancer and as antipsychotic and analgesic agents.

SUMMARY OF THE INVENTION

It has been discovered herein that the ring forming step to produce the above compounds can be carried out with decreased reaction time with particular organic copper activator that is inexpensive, stable and readily available.

The invention herein in one embodiment denoted the first embodiment, is directed at a method for preparing a 2,5-dihydrofuran, comprising the step of effecting rearrangement of a vinyl oxirane into a 2,5-dihydrofuran using a particular organic copper activator.

The invention in a second embodiment is directed at a method of preparing a 2,5-dihydrothiophene, comprising the step of effecting rearrangement of a vinyl thiirane using a particular organic copper activator.

The invention in a third embodiment is directed at a method of forming a 2,5-dihydro-1H-pyrrole, comprising the step of effecting rearrangement of a vinyl aziridine, using a particular organic copper activator.

DETAILED DESCRIPTION

In general the methods of the first, second and third embodiments are directed to a method of preparing a compound having the structure

(A)

comprising the step of effecting rearrangement of

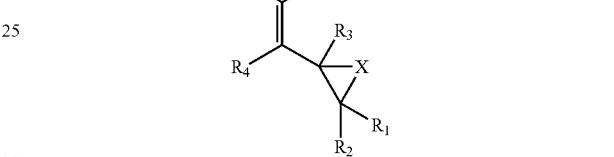

(B)

using an organic copper activator, where X is selected from the group consisting of O, S and NR where R is a protecting group or other valance balancing group since N is trivalent and where $R_1$, $R_2$, $R_3$, $R_4$, $R_5$ and $R_6$ are the same or different and are independently selected from the group consisting of hydrogen, $C_1$-$C_8$ alkyl, carbocyclic aryl group having 6 to 10 carbon atoms, heterocyclic aryl group having 6 to 10 carbon atoms, and halogen, and two or more of $R_1$, $R_2$, $R_3$, $R_4$, $R_5$ and $R_6$ can be bonded together to form a ring or rings.

We turn now to the first embodiment of the invention herein.

The vinyl oxiranes that are the substrates (starting materials) for the first embodiment herein have the formula

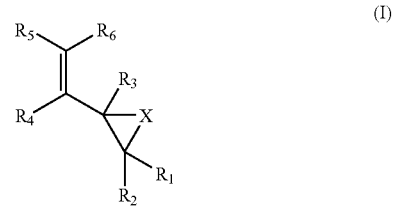

(I)

and the 2,5-dihydrofuran product has the formula

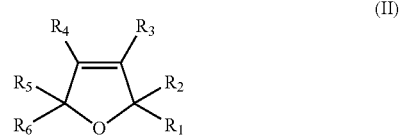

(II)

where $R_1$, $R_2$, $R_3$, $R_4$, $R_5$ and $R_6$ are the same or different and are independently selected from the group consisting of hydrogen, $C_1$-$C_8$ alkyl, carbocyclic aryl group having 6 to 10 carbon atoms, heterocyclic aryl group having 6 to 10 carbon atoms, and halogen, and two or more of $R_1$, $R_2$, $R_3$, $R_4$, $R_5$ and $R_6$ can be bonded together to form a ring or rings.

The term "carbocyclic aryl group" is used herein to mean a group containing one or more rings where all of the ring atoms are carbon atoms including but not limited to phenyl, naphthyl, indanyl, indenyl and the like.

The term "heterocyclic aryl group" is used herein to mean a group containing one or more rings where at least one ring contains 1 to 3 heteratoms, with the remainder of the ring atoms being carbon atoms. The heteroatom(s) is oxygen, sulfur or nitrogen. Examples of heterocyclic aryl groups are pyridyl, pyrrolyl, imidazolyl, thiazolyl, furanyl, quinolinyl, and the like.

Specific vinyl oxiranes used in experiments herein include 3,4-epoxy-2-hexyl-1-butene (used in Working Examples 1-16 herein); 3,4-epoxy-3-hexyl-1-butene (used in Working Examples 17 and 18 herein); 1,2-epoxy-3-undecene (used in Working Examples 19 and 20 herein); trans-3,4-epoxy-1-undecene (used in Working Example 21 herein); 4-butyl-3,4-epoxy-1-octene (used in Working Example 22 herein); 3,4-epoxy-1-butene (used in Example XXIV hereinafter), 3,4-epoxy-2- or -3-methyl-1-butene and 1,2-epoxy-3-pentene or 3,4-epoxy-1-pentene (used in making 3-methyltetrahydrofuran and 2-methyltetrahydrofuran in Examples XXV and XXVI hereinafter).

The vinyl oxiranes can be made by well known methods, e.g., as described in Olofsson, B. and Somfai, P., "Aziridines and Epoxides in Organic Synthesis", Yudin, A. K., Editor, Wiley-VCH, Weinheim, Germany; pages 316-347 (2006); and Matteson, D. S., Tetrahedron Lett. 27, 795-798 (1986).

We turn now to the organic copper catalyst activators used in method of the first embodiment. These are selected from the group consisting of

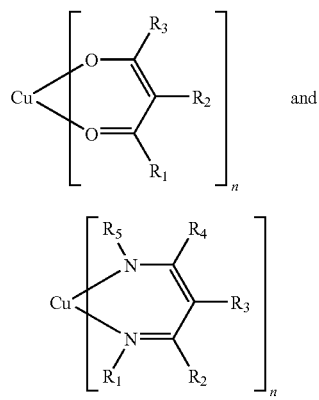

and mixtures thereof, where $R_1$, $R_2$, $R_3$, $R_4$ and $R_5$ are the same or different and are independently selected from the group consisting of $C_1$-$C_8$ alkyl which is unsubstituted or which is substituted with one or more of halogen or $C_6$-$C_{20}$ aryl; trifluoromethyl; and phenyl which is unsubstituted or substituted with but not limited to fluoro, trifluoromethyl, $C_1$-$C_8$ alkyl or $C_6$-$C_{20}$ aryl; and two or more of $R_1$, $R_2$, $R_3$, $R_4$ and $R_5$ can be bonded together to form a ring or rings; and n is 1 or 2.

Specific catalysts have the structures (III) are: (1) where $R_1$ and $R_3$ are $CF_3$ and $R_2$ is H and n=2 (denoted Cu (hfacac)$_2$), used in Working Examples 1-10 and 17-23 herein and in Examples XXIV, XXV and XXVI; (2) where $R_1$ is $CH_3$, $R_2$ is H, and $R_3$ is $CF_3$ and n=2 (denoted Cu(tfacac)$_2$), used in Working Example 11 herein; (3) where $R_1$ and $R_3$ are $CH_3$ and $R_2$ is H and n=2 (denoted Cu(acac)$_2$), used in Working Example 12 herein; (4) where $R_1$ and $R_3$ are $CF_3$ and $R_2$ is H, and n=1, complexed with bis(trimethylsilyl)acetylene (denoted Cu(hfacac) (TMS-≡-TMS), used in Working Example 13 herein); (5) where $R_1$ and $R_3$ are 4-trifluoromethylphenyl and $R_2$ is H and n=2 (denoted Cu(ptfm)$_2$, used in Working Example 14 herein); (6) where $R_1$ and $R_3$ are 4-fluorophenyl and $R_2$ is H and n=2 (denoted Cu(Pf)$_2$, used in Working Example 15 herein); (7) where $R_1$ and $R_3$ are phenyl and $R_2$ is H and n=2 (denoted Cu(dbm)$_2$), used in Working Example 16 herein); (8) where $R_1$ and $R_2$ are joined together as $(CH_2)_4$ to form a ring and $R_3$ is $CH_3$ and n=2 (denoted Cu(accy)$_2$) used in Table 1 herein; (9) where $R_1$ and $R_2$ are joined together as $(CH_2)_4$ to form a ring and $R_3$ is $CF_3$ and n=2 (denoted Cu(tfaccy)$_2$) used in Table 1 herein; and (10) where $R_1$ is $C_4H_9$, $R_2$ is H, and $R_3$ is $C_3H_7$ (denoted Cu(fod)$_2$) used in Table 1 herein.

The catalysts (III) are made by reacting diketone having the formula

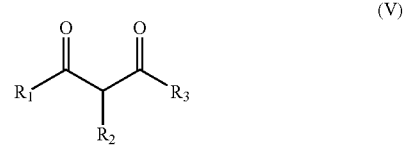

with Cu(OAc)$_2$, Cu(OAc) or an appropriate Cu(I) or Cu(II) salt depending on whether n=1 or 2. The catalyst Cu (hfacac)$_2$ is available commercially as is copper 1,3-diphenyl-1,3-propanedionate (Cu (dbm)$_2$). Also, [bis(trimethylsilyl)acetylene](hexafluoroacetylacetonate)copper (I) is commercially available. The catalyst Cu(ptfm)$_2$ is compound 41 in Supporting Information for Batory, L. A., et al., J. Am. Chem. Soc. 128, 16054-16055 (2006) and is depicted and made as described therein. The structures of catalysts Cu(accy)$_2$ and Cu(tfaccy) are depicted on page S16 in Supporting Information for Batory, L. A., et al., J. Am. Chem. Soc. 128, 16054-16055 (2006). Cu(accy)$_2$ is made as described in King, N. J., Jr., et al., J. Org. Chem. 32, 1691-1692 (1967). Cu(tfaccy)$_2$ is made as described in Ebraheem, K. A. K., et al., Canadian Journal of Spectroscopy 28, 9-13 (1983) and Hamdi, S. J., Monatsh Chem. 123, 1081-1082 (1999). Cu(tfacac)$_2$, Cu(acac)$_2$ and Cu(tfacac)BTMSA are commercially available.

The catalyst (IV) can be made by reacting the diketone (V) with a primary amine to form diimine compound

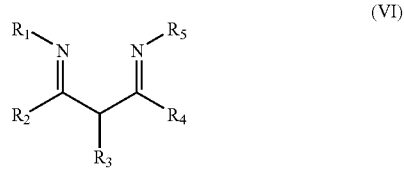

and reacting (VI) with a source of Cu (I) or Cu (II).

Copper catalyst loading can range for example from 0.01 mol % to 40 mol % (vinyl oxirane basis), e.g., 0.1% to 5 mol % (vinyl oxirane basis).

The reactions of the method of the first embodiment can be carried out in a solvent which dissolves the vinyl oxirane and the catalyst, e.g., benzene, toluene, xylene, ethylacetate, acetone, 1,4-dioxane, or 1,2-dichloroethane. The substrate can be present in the solvent at a concentration ranging, for example, from 0.01 M to 10 M; neat reactions are discussed below.

Examples of the reaction of the first embodiment are set forth in Working Examples I-XXVI hereinafter.

Examples of reactions of the first embodiment are also set forth in entries 6-15 of Table 1 below:

TABLE 1

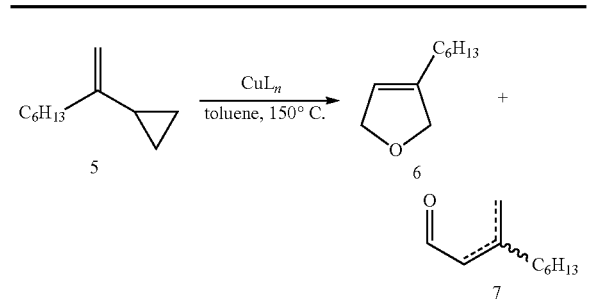

| entry | catalyst[b] | mol % | time (h) | 6:7[c] |
|---|---|---|---|---|
| 1 | Cu powder | 100 | 14 | no rxn |
| 2 | Cu(OAc)$_2$ | 10 | 14 | no rxn |
| 3 | CuCl$_2$ | 10 | 14 | >1:20 |
| 4 | CuSO$_4$•5H$_2$O | 10 | 14 | >1:20 |
| 5 | Cu(TFA)$_2$ | 10 | 15 | 1:8 |
| 6 | Cu(acac)$_2$ | 5 | 17 | 5:1 |
| 7 | Cu(tfacac)$_2$ | 5 | 2 | 12:1 |
| 8 | Cu(hfacac)$_2$ | 5 | 0.25 | 13:1 |
| 9 | Cu(hfacac)$_2$ | 1 | 2 | 17:1 |
| 10 | Cu(hfacac)(BTMSA) | 5 | 4 | 15:1 |

TABLE 1-continued

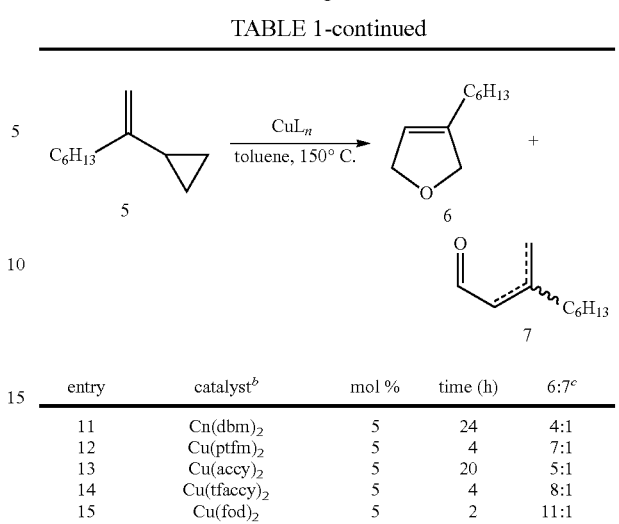

| entry | catalyst[b] | mol % | time (h) | 6:7[c] |
|---|---|---|---|---|
| 11 | Cn(dbm)$_2$ | 5 | 24 | 4:1 |
| 12 | Cu(ptfm)$_2$ | 5 | 4 | 7:1 |
| 13 | Cu(accy)$_2$ | 5 | 20 | 5:1 |
| 14 | Cu(tfaccy)$_2$ | 5 | 4 | 8:1 |
| 15 | Cu(fod)$_2$ | 5 | 2 | 11:1 |

[a]Reactions are performed in a sealed tube in toluene at 150° C. with the specified catalyst loading.
[b]See ref 9.
[c]Based on molar ratios as determined from NMR integration.

In Table 1, BTMSA means bis(trimethylsilylacetylene).

The substrate for 5 depicted in Table 1 above was made as described at page S3 of Supporting Information for Batory, L. A., et al. J. Am. Chem. Soc. 128, 16054-16055 (2006). The rearrangement of substrate 5 is shown in description of compound 6 of that Supporting Information.

Still other examples of reactions of the first embodiment are set forth in Table 2 below:

TABLE 2

| entry | substrate | product | mol % | time (h) | DHF: Ald/Ket | yield |
|---|---|---|---|---|---|---|
| 1 | (C$_6$H$_{13}$, epoxide) | C$_6$H$_{13}$-DHF | 0.5 | 2 | 17:1 | 94% |
| 2 | (vinyl epoxide, C$_6$H$_{13}$) | C$_6$H$_{13}$-DHF | 0.5 | 2 | 5:1 | 59% |
| 3 | C$_7$H$_{15}$-CH=CH-epoxide | C$_7$H$_{15}$-DHF | 5[b] | 2 | 16:1 | 86% |
| 4 | vinyl epoxide-C$_7$H$_{15}$ | C$_7$H$_{15}$-DHF | 1 | 20 | 3:1 | 60% |
| 5 | (p-MeC$_6$H$_4$, epoxide) | p-MeC$_6$H$_4$-DHF | 1 | 1 | 10:1 | 88% |
| 6 | vinyl epoxide-(C$_4$H$_9$)$_2$ | DHF-(C$_4$H$_9$)$_2$ | 5 | 48 | >20:1 | 92% |

TABLE 2-continued

| entry | substrate | product | mol % | time (h) | DHF: Ald/Ket | yield |
|---|---|---|---|---|---|---|
| 7 | C₄H₉ on vinyl oxirane with C₄H₉ groups | C₄H₉-substituted aldehyde | 5 | 0.25 | >20:1 | 95% |
| 8 | isopropenyl methyl oxirane | 3,4-dimethyl-2,5-dihydrofuran | 0.5 | 2 | 13:1 | 93%[c] |
| 9 | ethyl vinyl oxirane with C₇H₁₅ | 3-ethyl-2-C₇H₁₅-2,5-dihydrofuran | 5 | 2 | >20:1 | 97% |
| 10 | cycloheptene oxide (bicyclic) | bicyclic dihydrofuran | 5 | 24 | 10:1 | 91%[c] |
| 11 | cyclooctene oxide (bicyclic) | bicyclic dihydrofuran | 5 | 4 | >20:1 | 72% |

[a]Reactions are performed in a sealed tube in toluene at 150° C. with Cu(hfacac)₂ at the specified loading.
[b]Cu(tacac)₂ is the catalyst.
[c]Volatile compound; yield based on molar ratios from NMR integration.

The substrate for entry 1 is the same as for the substrate for Table 1. With reference to the Supporting Information of Batory, L. A., et al., J. Am. Chem. Soc. 128, 16054-16055 (2006), the substrate for entry 2 of Table 2 is that for compound 14; the synthesis of substrate for entry 3 of Table 2 is that for compound 10; for entry 4 of Table 2, that of compound 17; for entry 5 of Table 2, that for compound 21; for entry 6 of Table 2, that for compound 27; for entry 7 of Table 2, that for compound 30; for entry 8 of Table 2, that for compound 31; for entry 9 of Table 2, that for compound 36.

With reference to said Supporting Information, the product for entries 1 and 2, is compound 6; the product for entry 3, is compound 11; the product for entry 5, is compound 22; the product for entry 6, is compound 28; the product for entry 8, is compound 31; the product for entry 9 is compound 37; and the products for entries 10 and 11 are respectively compounds 38 and 39.

Entry 7 doesn't rearrange to 2,5-dihydrofuran, probably because of steric hindrance; thus exceptions to the first embodiment are where steric hindrance prevents formation of (II).

The reaction can also be carried out neat.

In one example of the reaction being carried out neat, the catalyst is added to and dissolved in the vinyl oxirane substrate (all the simple vinyl oxiranes are liquid) and the heating of the solution is carried out to provide the reaction.

Oxiranes 5 and 10 of Table 2 were successfully rearranged in the absence of solvent with reaction carried out with 1 mol % Cu(hfacac)₂ at 150° C. for 30 minutes to provide 96% yield of rearranged product in the case of oxirane 5 and 87% yield of rearranged product in the case of oxirane 10.

In the first embodiment, the temperature of reaction can range, for example, from 50 to 300° C. In the case of reactions in solvent, operational temperatures are, for example, 100 to 150° C.

Conversion to corresponding tetrahydrofuron is carried out by hydrogenation (i.e., to add the hydrogen) of the 2,5-dihydrofuran product of the first embodiment. This can be carried out by reaction with hydrogen gas, for example, in the presence of platinum or palladium hydrogenation catalyst, e.g., on finely divided carbon.

In cases for special mention, 2-methyl-2,5-dihydrofuran is converted to 2-methyltetrahydrofuran and 3-methyl-2,5-dihydrofuran is converted to 3-methyltetrahydrofuran by catalytic reduction of the 2,5-dihydrofuran as described above.

In one case epoxidation of isoprene gives a vinyl oxirane which is converted to 3-methyl-2,5-dihydrofuran by the method of the first embodiment and the 3-methyl-2,5-dihydrofuran is converted to 3-methyltetrahydrofuran. The vinyl oxirane has the structural formula

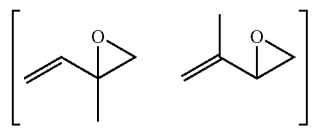

The 3-methyl-2,5-dihydrofuran has the structural formula

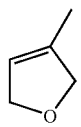

and the 3-methyltetrahydrofuran has the structural formula

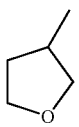

In another case, epoxidation of piperylene gives a vinyl oxirane which is converted to 2-methyl-2,5-dihydrofuran by the method of the first embodiment herein, which then is converted to 2-methyltetrahydrofuran. The vinyl oxirane has the structural formula

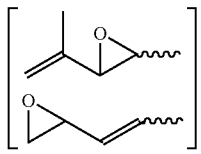

The 2-methyl-2,5-dihydrofuran has the structural formula

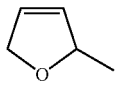

and the 2-methyltetrahydrofuran has the formula

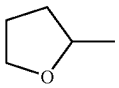

We turn now to the second embodiment herein.

The vinyl thiiranes for the substrates (starting materials) for the second embodiment have the formula:

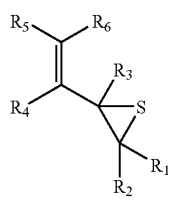

VII and the 2,5-dihydrothiophene product has the formula

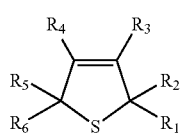

VIII where $R_1$, $R_2$, $R_3$, $R_4$, $R_5$ and $R_6$ are the same or different and are independently selected from the group consisting of hydrogen, $C_1$-$C_8$ alkyl, carbocyclic aryl group having 6 to 10 carbon atoms, heterocyclic aryl group having 6 to 10 carbon atoms, and halogen, and two or more of $R_1$, $R_2$, $R_3$, $R_4$, $R_5$ and $R_6$ can be bonded together to form a ring or rings.

The terms "carbocyclic aryl group" and "heterocyclic aryl group" have the same definitions as set forth above for the first embodiment.

Specific vinyl thiiranes used in experiments herein are set forth in Tables 3 and 4 below.

The vinyl thiirane substrates can be prepared from vinyl oxiranes as described in Bordwell, F. G., et al., J. Am. Chem. Soc. 75, 4959-4962 (1953) and Price, C. C., et al., J. Am. Chem. Soc. 75, 2396-2400 (1953) or by reduction of enone-thiophosphates as described in Maciagiewicz, I., et al., Tetrahedron Lett., 40, 3791-3794 (1999).

The organic copper catalyst activators are the same as for the first embodiment. Copper catalyst loading can range, for example, from 0.01 mol % to 40 mol % (vinyl thiirane basis), e.g., 0.1 to 30 mol %.

The reactions of the second embodiment can be carried out in a solvent which dissolves the vinyl thiirane and the catalyst, e.g. benzene, toluene, xylene, ethyl acetate, acetone, 1,4-dioxane or 1,2-dichloromethane.

These reactions can also be carried out neat.

Examples of reactions of the second embodiment are set forth in entries 9-11 of Table 3 below:

TABLE 3

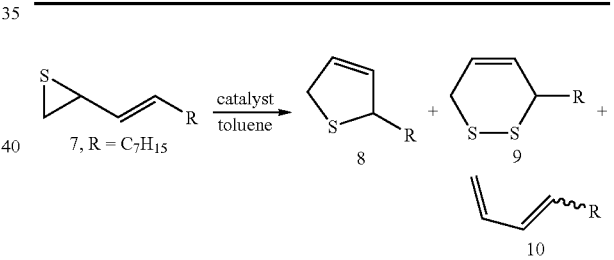

| entry | catalyst | time (h)[a] | 8:9:10[b] |
|---|---|---|---|
| 1 | none | 12 | 0:0:1 |
| 2 | Cu | 12 | 0:0:1 |
| 3 | CuBr | 2 | 1:9:10 |
| 4 | Cu(OAc)$_2$ | 2 | 0:1:3 |
| 5 | Cu(TFA)$_2$ | 2 | 0:1:1 |
| 6 | Cu(thiophene 2-carboxylate) | 2 | 0:2:3 |
| 7 | Cu(cyclohexanebutyrate)$_2$ | 2 | 1:4:8 |
| 8 | Cu(2-ethylhexanoate)$_2$ | 2 | 1:3:4 |
| 9 | Cu(acac)$_2$ | 3 | 1:6:8 |
| 10 | Cu(tfacac)$_2$ | 3 | 2:0:3 |
| 11 | Cu(hfacac)$_2$ | 1 | 11:0:1 |

[a]100% conversion at 5 mol % catalyst, 120° C. and 0.01 M in toluene.

[b]Ratio of products is determined by analyzing crude $^1$H-NMR spectra.

Additional examples of reaction of the second embodiment are set forth in Table 4 below:

TABLE 4

| entry | substrate | product | mol % | t (h) | T (° C.) | yield[a] |
|---|---|---|---|---|---|---|
| 1 | S-cyclopropane-CH=CH$_2$, C$_6$H$_13$ | 2,5-dihydrothiophene, C$_6$H$_{13}$ | 1<br>0.1<br>10 | 0.5<br>1.7<br>40 | 80<br>80<br>25 | 93%<br>95%[b]<br>95%[b] |
| 2 | substrate with C$_6$H$_{13}$ | product with C$_6$H$_{13}$ | 1 | 1 | 100 | 95% |
| 3[c] | substrate with C$_7$H$_{15}$ | product with C$_7$H$_{15}$ | 5 | 3 | 120 | 85% |
| 4[b] | substrate with C$_7$H$_{15}$ | product with C$_7$H$_{15}$ | 5 | 1.5 | 120 | 78% |
| 5 | substrate with p-MeC$_6$H$_4$ | product with p-MeC$_6$H$_4$ | 2 | 2 | 80 | 85% |
| 6 | substrate with C$_6$H$_{13}$ | product with C$_6$H$_{13}$ | 10 | 20 | 80 | 75% |
| 7 | substrate with C$_5$H$_{11}$ | product with C$_5$H$_{11}$ | 10 | 20 | 80 | 92% |
| 8[d] | cyclohexenyl thiirane | hexahydrobenzothiophene | 30 | 24 | 100 | 65% |
| 9 | substrate with C$_5$H$_{11}$, C$_6$H$_{13}$ | product with C$_5$H$_{11}$, C$_6$H$_{13}$ | 10 | 4.5 | 80 | 65% |

Conditions: Cu(hfacac)$_2$, C$_6$H$_6$, 0.1 M
[a] isolated yield,
[b] yield based on molar ratios from $^1$H-NMR integration,
[c] 0.01 M,
[d] Cu(tfacac)$_2$ With reference to the Supporting Information for Rogers, E., et al., J. Am. Chem. Soc. 129, cited below, the making of compound 7 of Table 3 is described at pages S1 and S2; the making of compound 8 is described at S2; the substrate for entry 1 of Table 3 is compound 22; the reaction of entry 1 of Table 4 to produce 23 is set forth at S3; the substrate for entry 2 of Table 4 is compound 24 at page S4; the substrate for entry 3 of Table 4 is compound 25 at S4; the substrate for entry 5 of Table 4 is compound 26; the reaction of entry 5 of Table 4 to produce 27 is set forth at S5; the substrate for entry 7 of Table 4 is compound 32 at S7 and the reaction of entry 7 of Table 4 to produce 33 is set forth at S8; substrate for entry 8 in Table 4 is compound 34 at S8 and the reaction of entry 7 to produce compound 25 is set forth at S9; and finally the substrate for entry 9 is compound 37 at s9 and the reaction of entry 9 produces product 38 at S10.

In the second embodiment, if solvent is present, the concentration of substrate in the solvent preferably ranges from 0.01 to 5 M.

In the second embodiment the temperature can range, for example, from 20 to 125° C.

The 2,5-dihydrothiophene products of the second embodiment can be converted to the corresponding tetrahydrothiophenes by reduction of the 2,5-dihydrothiophene, e.g. by hydrogenation of hydrogen gas in the presence of platinum or palladium hydrogenation catalyst, e.g. on finely divided carbon.

We turn now to the third embodiment herein.

The vinyl aziridines for the substrate (starting materials) for the third embodiment are N-protected aziridines having the formula

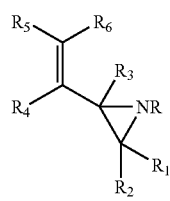

IX and the 2,5-dihydro-1H-pyrrole product has the formula

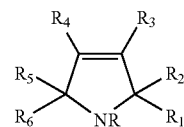

Where R is an N-protecting group and $R_1$, $R_2$, $R_3$, $R_4$, $R_5$ and $R_6$ are the same or different and are independently selected from the group consisting of hydrogen, $C_1$-$C_8$ alkyl, carbocyclic aryl group having 6 to 10 carbon atoms, heterocyclic aryl group having 6 to 10 carbon atoms, and halogen, and two or more of $R_1$, $R_2$, $R_3$, $R_4$, $R_5$ and $R_6$ can be bonded together to form a ring or rings.

The terms "carbocyclic aryl group" and "heterocyclic aryl group" have the same definitions as set forth above for the first embodiment.

The N-protecting group is present because aziridines are best synthesized containing an N-protecting group. The aziridines herein were synthesized as p-toluene sulforamide (tosyl) N-protected aziridines and as phthalimide N-protected aziridines.

Specific vinyl aziridines used in experiments herein are set forth in Tables 5 and 6 below.

The tosyl protected azaridines are prepared by the Sharpless aziridination protocol as described in Jeong, J. U., et al., J. Am. Chem. Soc. 120, 6844 (1998) or via nitrenes generated from tosyl phenyliodinanes as described in Evans, D. A., et al., J. Am. Chem. Soc. 116, 2742 (1994). The phthalimide protected aziridines are prepared as described in Atkinson R. S., et al., Chem. Commun. 1230 (1967); and Siu T., et al., J. Am. Chem. Soc. 124, 530 (2002); and Yang, K. S., et al., Org. Lett. 4, 1107 (2002).

The organic copper catalyst activators are the same as for the first embodiment. Copper catalyst loading can range, for example, from 0.01 mol % to 40 mol % (protected vinyl aziridine basis), e.g. 5 to 15 mol %. The reaction of the third embodiment can be carried out in a solvent which dissolves the protected vinyl aziridine and the catalyst, e.g. benzene, toleuene, xylene, ethyl acetate, acetone, 1,4-diokane or 1,2-dichloromethane or neat.

Examples of reactions of the third embodiment where the protected aziridine is tosyl protected are set forth in Table 5 below:

TABLE 5

| Entry | Substrate | Product | Time(h) | T (° C.) | Yield |
|---|---|---|---|---|---|
| 1 | | | 2 | 110 | 99% |
| 2 | | | 3 | 60 | 99% |
| 3 | | | 2 | 80 | 99% |
| 4 | | | 2 | 110 | 99% |
| 5 | | | 1 | 60 | 99% |
| 6 | | | 6 | 120 | 99% |

TABLE 5-continued

| Entry | Substrate | Product | Time(h) | T (° C.) | Yield |
|---|---|---|---|---|---|
| 7 | [structure: RN-aziridine with Ph, Ph, and vinyl-Ph] | [structure: pyrrole with Ph, Ph] | 20 | 110 | 99% |
| 8 | [structure: RN-aziridine with Ph, Ph, vinyl-Ph] | [structure: pyrrole with Ph, Ph] | 13 | 135 | 99% |
| 9 | [structure: RN-aziridine dimethyl with isopropenyl] | [structure: pyrrole dimethyl methyl] | 12 | 135 | 99% |
| 10 | [structure: RN-aziridine with OTBS vinyl and OTBS] | [structure: pyrrole OTBS] | 12 | 100 | 99% |
| 11 | [structure: bicyclic aziridine from cycloheptene] | [structure: bridged bicyclic NR] | 8 | 135 | 5% |
| 12 | [structure: bicyclic aziridine from cyclooctene] | [structure: bridged bicyclic NR] | 10 | 150 | 90% |

Conditions: 10% Cu(hfacac)$_2$, toluene;

In Table 5, R is tosyl (Ts).

Examples of reaction of the third embodiment where the protected aziridine is phthalimide protected are set forth in Table 6 below:

TABLE 6

| Entry | Substrate[a] | Product | Time (h) | T(° C.) | Yield |
|---|---|---|---|---|---|
| 1 | [structure: RN-aziridine with vinyl] | [structure: pyrrole] | 12 | 100 | 99% |
| 2[b] | [structure: RN-aziridine methyl vinyl] | [structure: methyl pyrrole] | 12 | 100 | 99% |
| 3[b] | [structure: RN-aziridine with isopropenyl] | [structure: methyl pyrrole] | 12 | 100 | 99% |
| 4 | [structure: RN-aziridine dimethyl isopropenyl] | [structure: dimethyl methyl pyrrole] | 4 | 80 | 99% |
| 5 | [structure: RN-aziridine methyl vinyl] | [structure: methyl pyrrole] | 14 | 100 | 99% |
| 6 | [structure: bicyclic aziridine cycloheptene] | [structure: bridged bicyclic NR] | 12 | 150 | 70% |
| 7 | [structure: bicyclic aziridine cyclooctene] | [structure: bridged bicyclic NR] | 20 | 150 | 90% |
| 8 | [structure: bicyclic aziridine cyclohexene] | [structure: bridged bicyclic NR] | 10 | 150 | 40% |

Conditions: 10% Cu(hfacac)$_2$, toluene;
[a]Reaction times, temperature and yields have not beem optimized,
[b]rearranged together as a mixture In Table 6, R is phthalimide.

In the third embodiment, if solvent is present, the concentration of the substrate in solvent ranges, for example, from 0.01 M to 10 M.

In the third embodiment the reaction temperature can range, for example, from 30° C. to 300° C., e.g., from 50° to 200° C. or 60° C. to 150° C.

The 2,5-dihydro-1H-pyrrole products of the third embodiment can be converted to the corresponding pyrrolidnes by hydrogenation with hydrogen gas in the presence of platinum or palladium hydrogenation catalyst, e.g., or fully divided carbon.

Removal of nitrogen protecting group is at least partly carried out by the hydrogenation and can be completely carried out using stronger reducing agent, e.g. trifluoroacetic acid (TFA) or tributylphosphine.

Elements of the invention and working examples are disclosed in Batory, L. A., et al., J. Am. Chem. Soc. 128, 16054-16055 (2006) and in Supporting Information therefor, the whole of which are incorporated herein by reference, and in Rogers, E., et al., J. Am. Chem. Soc. 129, published so for only on journal website and in Supporting Information therefor. Therefore, the whole of which is incorporated herein by reference. The Rogers et al. article is entitled "Highly Selective Copper-Catalyzed Ring Expansion of Vinyl Thiiranes: Application to Synthesis of Biotin and the Heterocyclic Core of Plavix®".

The following examples are illustrative for the invention.

Examples I-IV show the effect of Cu(hfacac)$_2$ loading on reaction. Examples V-VIII show effect of variation of solvent on reaction. Examples IX and X show effect of temperature on reaction. Examples XI-XVI show effect of variation in a catalyst on reaction. Examples XVII-XXIII demonstrate the effect of substitution on substrate, on reaction. Example XXV shows conversion of 2,5-dihydrofuran product to tetrahydrofuran. Example XXV shows preparation of 3-methyltetrahydrofuran. Example XXVI shows preparation of 2-methyltetrahydrofuran. Examples XXVII-XXXV are directed to reactions of the second embodiment herein.

WORKING EXAMPLE I

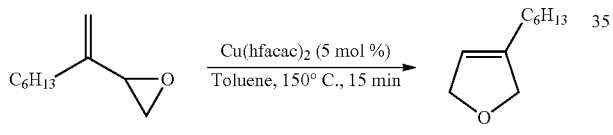

A stock solution of 0.122 g (0.792 mmol) substrate in 2.7 mL toluene was prepared. A stock solution of 0.020 g (0.042 mmol) of copper (II) hexafluoroacetylacetonate in 3 mL toluene was prepared. To a 13×100 mm culture tube was added 0.50 mL of the substrate solution, followed by 0.50 mL of the catalyst solution. The septa was replaced with a cap, and the seal was reinforced with Teflon tape. The tube was put in a 150° C. oil bath, and after 15 minutes, the reaction was removed and cooled. The solvent was removed in vacuo. The crude mixture was analyzed by $^1$H NMR spectroscopy and found to have a product ratio of 13:1 dihydrofuran to aldehyde.

WORKING EXAMPLE II

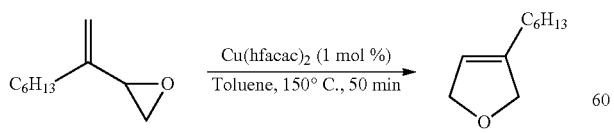

A stock solution of 0.122 g (0.792 mmol) substrate in 2.7 mL toluene was prepared. A stock solution of 0.020 g (0.042 mmol) of copper (II) hexafluoroacetylacetonate in 3 mL toluene was prepared. A second catalyst stock solution was then prepared from 0.6 mL of the first solution and 2.4 mL of toluene. To a 13×100 mm culture tube was added 0.50 mL of the substrate solution, followed by 0.50 mL of the catalyst solution. The septa was replaced with a cap, and the seal was reinforced with Teflon tape. The tube was put in a 150° C. oil bath, and after 50 minutes, the reaction was removed and cooled. The solvent was removed in vacuo. The crude mixture was analyzed by $^1$H NMR spectroscopy and found to have a product ratio of 16:1 dihydrofuran to aldehyde.

WORKING EXAMPLE III

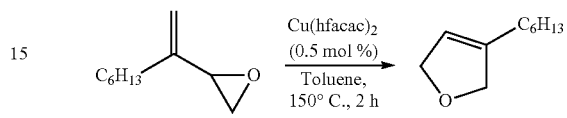

A stock solution of 0.122 g (0.792 mmol) substrate in 2.7 mL toluene was prepared. A stock solution of 0.014 g (0.029 mmol) of copper (II) hexafluoroacetylacetonate in 2 mL toluene was prepared. A second catalyst stock solution was then prepared from 0.3 mL of the first solution and 2.7 mL of toluene. To a 13×100 mm culture tube was added 0.50 mL of the substrate solution, followed by 0.50 mL of the second catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 17:1 dihydrofuran to aldehyde.

WORKING EXAMPLE IV

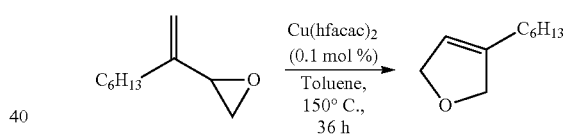

A stock solution of 0.100 g (0.649 mmol) substrate in 2.2 mL toluene was prepared. A stock solution of 0.021 g (0.044 mmol) of copper (IU) hexafluoroacetylacetonate in 3 mL toluene was prepared. A second catalyst stock solution was then prepared from 0.50 mL of the first solution and 2.0 mL of toluene. A third stock solution was then made from 0.3 mL of the second and 2.7 mL toluene. To a 13×100 mm culture tube was added 0.50 mL of the substrate solution, followed by 0.50 mL of the third catalyst solution. The septa was replaced with a cap, and the seal was reinforced with Teflon tape. The tube was put in a 150° C. oil bath, and after 30 hours, the reaction was removed and cooled. The solvent was removed in vacuo. The crude mixture was analyzed by $^1$H NMR spectroscopy and found to have a product ratio of 21:1 dihydrofuran to aldehyde.

WORKING EXAMPLE V

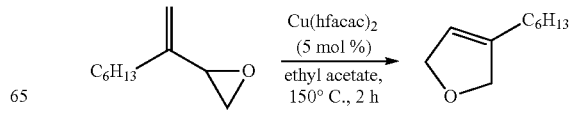

A stock solution of 0.020 g (0.13 mmol) substrate in 0.42 mL ethyl acetate was prepared. A stock solution of 0.014 g (0.029 mmol) of copper (II) hexafluoroacetylacetonate in 2 mL ethyl acetate was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 7:1 dihydrofuran to aldehyde.

WORKING EXAMPLE VI

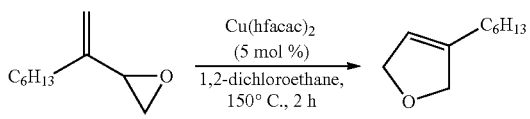

A stock solution of 0.020 g (0.13 mmol) substrate in 0.41 mL 1,2-dichloroethane was prepared. A stock solution of 0.013 g (0.027 mmol) of copper (II) hexafluoroacetylacetonate in 2 mL 1,2-dichloroethane was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 7:1 dihydrofuran to aldehyde.

WORKING EXAMPLE VII

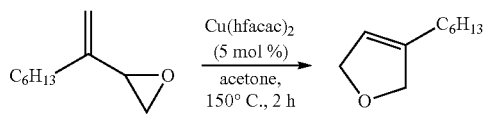

A stock solution of 0.018 g (0.12 mmol) substrate in 0.38 mL acetone was prepared. A stock solution of 0.014 g (0.029 mmol) of copper (II) hexafluoroacetylacetonate in 2 mL acetone was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 7:1 dihydrofuran to aldehyde.

WORKING EXAMPLE VIII

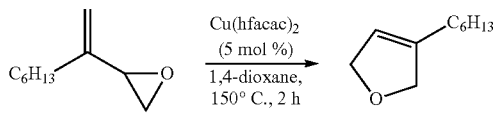

A stock solution of 0.019 g (0.12 mmol) substrate in 0.37 mL 1,4-dioxane was prepared. A stock solution of 0.014 g (0.029 mmol) of copper (I) hexafluoroacetylacetonate in 2 mL 1,4-dioxane was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 11:1 dihydrofuran to aldehyde.

WORKING EXAMPLE IX

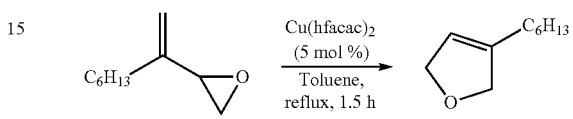

A stock solution of 0.121 g (0.79 mmol) substrate in 2.7 mL toluene was prepared. A stock solution of 0.021 g (0.044 mmol) of copper (II) hexafluoroacetylacetonate in 3 mL toluene was prepared. To a 1 dram vial equipped with a stir bar was added 0.50 mL of the substrate solution, followed by 0.50 mL of the catalyst solution. The vial was then connected to a condenser and placed in a 115° C. oil bath. The reaction was monitored by TLC and after approximately 1.5 hours, it was removed from the oil bath and cooled. The solvent was removed in vacuo. The crude mixture was analyzed by $^1$H NMR spectroscopy and found to have a product ratio of 15:1 dihydrofuran to aldehyde.

WORKING EXAMPLE X

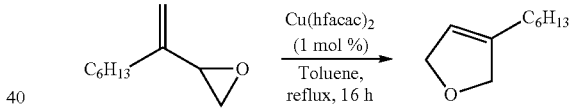

A stock solution of 0.061 g (0.40 mmol) substrate in 1.25 mL toluene was prepared. A stock solution of 0.014 g (0.029 mmol) of copper (II) hexafluoroacetylacetonate in 2.0 mL toluene was prepared. A second catalyst stock solution was then prepared from 0.20 mL of the first solution and 0.80 mL of toluene. To a 1 dram vial equipped with a stir bar was added 0.50 mL of the substrate solution, followed by 0.50 mL of the second catalyst solution. The vial was then connected to a condenser and placed in a was put in a 115° C. oil bath. After approximately 16 hours, it was removed from the oil bath and cooled. The solvent was removed in vacuo. The crude mixture was analyzed by $^1$H NMR spectroscopy and found to have a product ratio of 20:1 dihydrofuran to aldehyde.

WORKING EXAMPLE XI

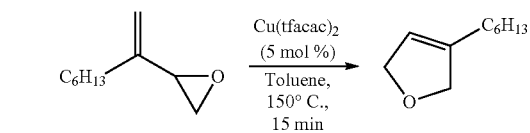

A stock solution of 0.121 g (0.79 mmol) substrate in 2.7 mL toluene was prepared. A stock solution of 0.016 g (0.043 mmol) of copper (II) trifluoroacetylacetonate in 3 mL toluene was prepared. To a 13×100 mm culture tube was added 0.50 mL of the substrate solution, followed by 0.50 mL of the catalyst solution. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy and found to have a product ratio of 12:1 dihydrofuran to aldehyde.

WORKING EXAMPLE XII

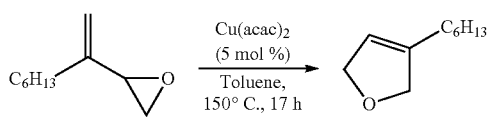

A stock solution of 0.687 g (4.46 mmol) substrate in 4.5 mL toluene was prepared. To a 13×100 nm n culture tube was added 0.0055 g (0.021 mmol) of copper (II) acetylacetonate, followed by 0.50 mL of the substrate solution and 2.5 mL toluene. The septa was replaced with a cap, and the seal was reinforced with Teflon tape. The tube was put in a 150° C. oil bath, and after 17 hours, the reaction was removed and cooled. The solvent was removed in vacuo. The crude mixture was analyzed by $^1$H NMR spectroscopy and found to have a product ratio of 5:1 dihydrofuran to aldehyde.

WORKING EXAMPLE XIII

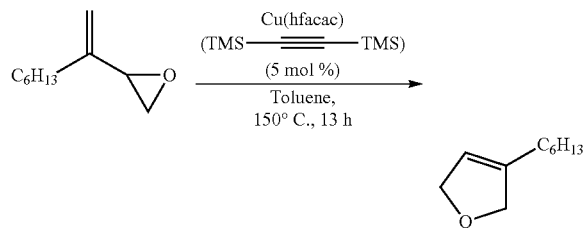

A stock solution of 0.048 g (0.312 mmol) substrate in 1.0 mL toluene was prepared. A stock solution of 0.013 g (0.0290 mmol) of [bis(trimethylsilyl)acetyylene] (hexafluoroacetylacetonato)copper (I) in 2.0 mL toluene was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 13 hours, the reaction was removed and cooled. The crude mixture was analyzed by $^1$H NMR spectroscopy and found to have a product ratio of 11:1 dihydrofuran to aldehyde.

WORKING EXAMPLE XIV

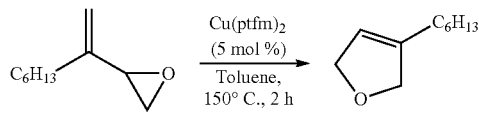

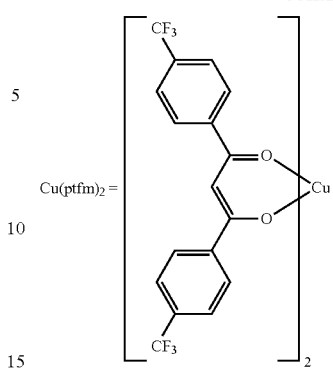

A stock solution of 0.163 g (1.06 mmol) substrate in 2.5 mL toluene was prepared. To a 13×100 mm culture tube was added 0.017 g (0.022 mmol) of copper (II) 1,3-bis(4-trifluoromethylphenyl)-1,3-propanedionate, followed by 1.00 mL of the substrate solution and 2.0 mL toluene. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy. The reaction was found to have achieved 84% conversion, with a product ratio of 11:1 dihydrofuran to aldehyde.

WORKING EXAMPLE XV

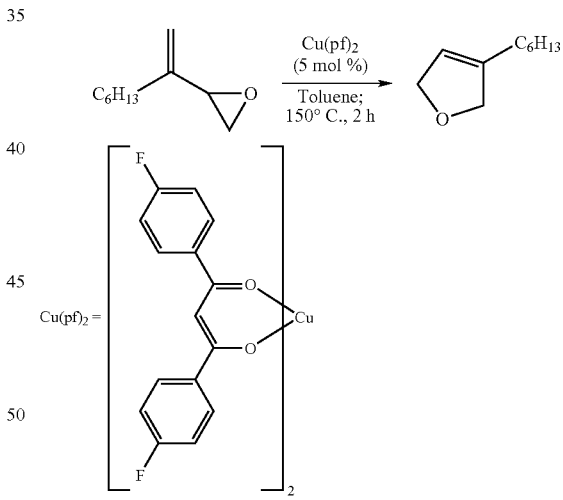

A stock solution of 0.163 g (1.06 mmol) substrate in 2.5 mL toluene was prepared. To a 13×100 mm culture tube was added 0.012 g (0.021 mmol) of copper (II) 1,3-bis(4-fluorophenyl)-1,3-propanedionate, followed by 1.00 mL of the substrate solution and 2.0 mL toluene. The septa was replaced with a cap, and the seal was reinforced with Teflon tape. The tube was put in a 150° C. oil bath, and 2 hours, the reaction was removed and cooled. The solvent was removed in vacuo. The crude mixture was analyzed by $^1$H NMR spectroscopy. The reaction was found to have achieved 11% conversion, with a product ratio of 3:1 dihydrofuran to aldehyde.

WORKING EXAMPLE XVI

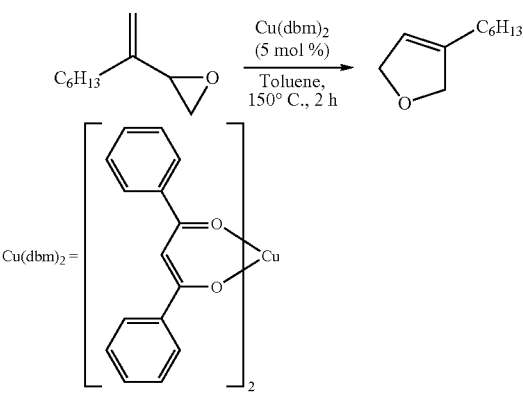

A stock solution of 0.363 g (2.36 mmol) substrate in 5.5 mL toluene was prepared. To a 13×100 mm culture tube was added 0.011 g (0.0216 mmol) of copper (II) 1,3-diphenyl-1,3-propanedionate, followed by 1.00 mL of the substrate solution and 2.0 mL toluene. The septa was replaced with a cap, and the seal was reinforced with Teflon tape. The tube was put in a 150° C. oil bath, and after 2 hours, the reaction was removed and cooled. The solvent was removed in vacuo. The crude mixture was analyzed by $^1$H NMR spectroscopy. The reaction was found to have achieved 17% conversion, with a product ratio of 6:1 dihydrofuran to aldehyde.

WORKING EXAMPLE XVII

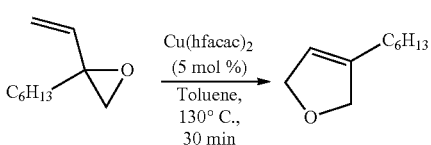

A stock solution of 0.039 g (0.25 mmol) substrate in 0.87 mL toluene was prepared. A stock solution of 0.024 g (0.050 mmol) of copper (II) hexafluoroacetylacetonate in 3.50 mL toluene was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 130° C. oil bath, and after 30 minutes, the reaction was removed and cooled. The solvent was removed in vacuo. The crude mixture was analyzed by $^1$H NMR spectroscopy and found to have a product ratio of 1:1 dihydrofuran to aldehyde.

WORKING EXAMPLE XVIII

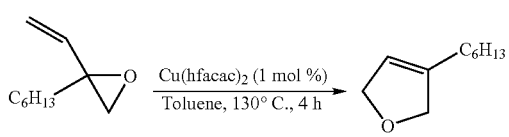

A stock solution of 0.039 g (0.25 mmol) substrate in 0.87 mL toluene was prepared. A stock solution of 0.024 g (0.050 mmol) of copper (II) hexafluoroacetylacetonate in 3.50 mL toluene was prepared. A second stock solution was then prepared from 0.4 mL of the first solution and 1.6 mL of toluene. To a 13×100 mm culture tube was added 0.25 mL of the substrate solution, followed by 0.25 mL of the second catalyst solution. The septa was replaced with a cap, and the seal was reinforced with Teflon tape. The tube was put in a 130° C. oil bath, and after 4 hours, the reaction was removed and cooled. The solvent was removed in vacuo. The crude mixture was analyzed by $^1$H NMR spectroscopy and found to have a product ratio of 4:1 dihydrofuran to aldehyde.

WORKING EXAMPLE XIX

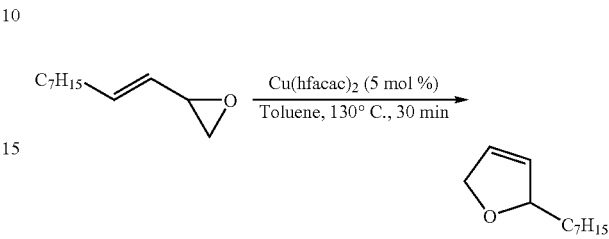

A stock solution of 0.043 g (0.26 mmol) substrate in 0.87 mL toluene was prepared. A stock solution of 0.024 g (0.050 mmol) of copper (II) hexafluoroacetylacetonate in 3.50 mL toluene was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 130° C. oil bath, and after 4 hours, the reaction was removed and cooled. The solvent was removed in vacuo. The crude mixture was analyzed by $^1$H NMR spectroscopy and found to have a product ratio of 2:1 dihydrofuran to aldehyde.

WORKING EXAMPLE XX

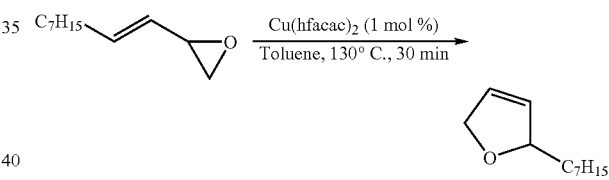

A stock solution of 0.043 g (0.26 mmol) substrate in 0.87 mL toluene was prepared. A stock solution of 0.0238 g (0.050 mmol) of copper (II) hexafluoroacetylacetonate in 1.56 mL toluene was prepared. A second catalyst stock solution was then prepared from 0.4 mL of the first solution and 1.6 mL of toluene. To a 13×100 mm culture tube was added 0.25 mL of the substrate solution, followed by 0.25 mL of the second catalyst solution. The septa was replaced with a cap, and the seal was reinforced with Teflon tape. The tube was put in a 130° C. oil bath, and after 4 hours, the reaction was removed and cooled. The solvent was removed in vacuo. The crude mixture was analyzed by $^1$H NMR spectroscopy and found to have a product ratio of 7:1 dihydrofuran to aldehyde.

WORKING EXAMPLE XXI

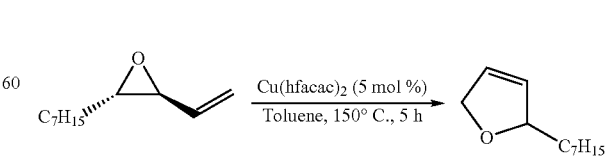

A stock solution of 0.030 g (0.18 mmol) substrate in 0.62 mL toluene was prepared. A stock solution of 0.020 g (0.042 mmol) of copper (II) hexafluoroacetylacetonate in 3.0 mL toluene was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 5 hours, the reaction was removed and cooled. The solvent was removed in vacuo. The crude mixture was analyzed by ¹H NMR spectroscopy and found to have a product ratio of 3:1 dihydrofuran to ketone.

WORKING EXAMPLE XXII

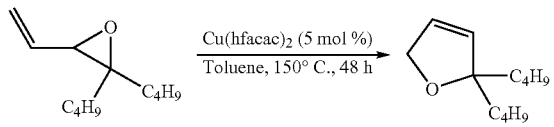

A stock solution of 0.032 g (0.17 mmol) substrate in 0.62 mL toluene was prepared. A stock solution of 0.014 g (0.029 mmol) of copper (II) hexafluoroacetylacetonate in 2.6 mL toluene was prepared. To a 13×100 mm culture tube was added 0.25 mL of the substrate solution, followed by 0.25 mL of the catalyst solution. The septa was replaced with a cap, and the seal was reinforced with Teflon tape. The tube was put in a 150° C. oil bath, and after 48 hours, the reaction was removed and cooled. The solvent was removed in vacuo. The crude mixture was analyzed by ¹H NMR spectroscopy and showed only the desired product.

WORKING EXAMPLE XXIII

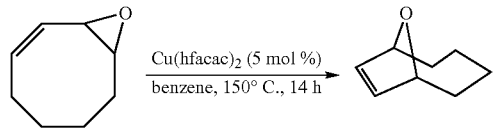

To a 13×100 mm culture tube was added 0.035 g (0.28 mmol) of substrate in 2.0 mL benzene followed by 0.0068 g (0.014 mmol) of copper (II) hexafluoroacetylacetonate. The tube was sealed and reinforced with Teflon tape. The tube was put in a 150° C. oil bath, and after 14 hours, the reaction was removed and cooled. The solvent was removed in vacuo. The crude mixture was analyzed by ¹H NMR spectroscopy and then hydrogenated to a known compound.

WORKING EXAMPLE XXIV

Preparation of 2,5-dihydrofuran and Tetrahydrofuran

Butadiene is converted to 3,4-epoxy-1-butene by metal catalyst epoxidation.

A stock solution of substrate (0.8 mmol) in 2.7 mL toluene is prepared. A stock solution of 0.04 mmol Cu(hfacac)₂ in 3 mL toluene is prepared. To a tube is added 0.5 mL of the substrate solution followed by 0.50 mL of the catalyst solution. Reaction is carried out in 150° C. oil bath. The 2,5-dihydrofuran product is purified. The 2,5-dihydrofuran product is hydrogenated using hydrogen gas and Pt or Pd catalyst, to produce tetrahydrofuran.

WORKING EXAMPLE XXV

Preparation of 3-Methyl Tetrahydrofuran

Isoprene is converted to 3,4-epoxy-2- and -3-methyl-1-butene by metal catalyzed epoxidation.

A stock solution of substrate (0.8 mmol) in 2.7 mL toluene is prepared. A stock solution of 0.04 mmol Cu(hfacac)₂ in 3 mL toluene is prepared. To a tube is added 0.5 mL of the substrate solution followed by 0.50 mL of the catalyst solution. Reaction is carried out in 150° C. oil bath. The 3-methyl-2,5-dihydrofuran product is purified. The 3-methyl-2,5-dihydrofuran product is hydrogenated using hydrogen gas and Pt or Pd catalyst, to produce tetrahydrofuran.

WORKING EXAMPLE XXVI

Preparation of 2-methyl Tetrhydrofuran

Piperylene is converted to 1,2-epoxy-3-pentene or 3,4-epoxy-1-pentene by metal catalyzed epoxidation.

A stock solution of substrate (0.8 mmol) in 2.7 mL toluene is prepared. A stock solution of 0.04 mmol Cu(hfacac)₂ in 3 mL toluene is prepared. To a tube is added 0.5 mL of the substrate solution followed by 0.50 mL of the catalyst solution. Reaction is carried out in 150° C. oil bath. The 2-methyl-2,5-dihydrofuran product is purified. The 2-methyl-2,5-dihydrofuran product is hydrogenated using hydrogen gas and Pt or Pd catalyst, to produce 2-methyltetrahydrofuran.

WORKING EXAMPLE XXVII

Preparation of 3-hexyl-2,5-dihydrothiophene

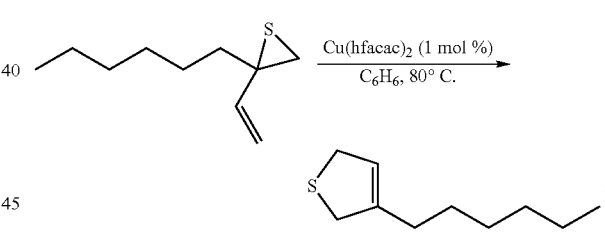

A solution of 1,2-epithio-2-hexyl-3-butene (40 mg, 0.24 mmol) and Cu(hfacac)₂ (1.2 mg, 2.4 µmol) in benzene (1 mL) was heated at 80° C. for 0.5 h in a pressure tube. Concentration of the solvent in vacuo afforded a residue, which was purified by column chromatography (n-pentane) to give 3-Hexyl-2,5-dihydrothiophene (37 mg, 93%) as a colorless oil.

WORKING EXAMPLE XXVIII

Preparation of 3-hexyl-2,5-dihydrothiophene

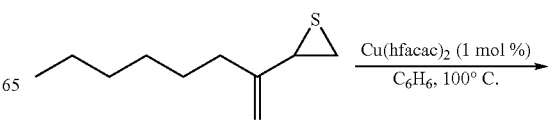

-continued

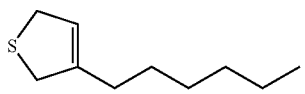

A solution of 1,2-epithio-3-hexyl-3-butene (40 mg, 0.24 miol) and Cu(hfacac)$_2$ (1.2 mg, 2.4 µmol) in benzene (1 mL) was heated at 100° C. for 1 h in a pressure tube. Concentration of the solvent in vacuo afforded a residue, which was purified by column chromatography (n-pentane) to give 3-Hexyl-2,5-dihydrothiophene (38 mg, 95%) as a colorless oil.

WORKING EXAMPLE XXIX

Preparation of 2,5-dihydro-3-(p-tolyl)thiophene

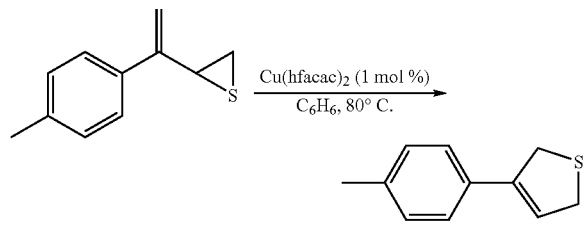

A solution of 1,2-epithio-3-p-tolyl-3-butene (40 mg, 0.23 mmol) and Cu(hfacac)$_2$ (1.1 mg, 2.3 µmol) in benzene (1 mL) was heated at 80° C. for 2 h in a pressure tube. Concentration of the solvent in vacuo afforded a residue, which was purified by column chromatography (n-pentane) to give 2,5-Dihydro-3-(p-tolyl)thiophene (34 mg, 85%) as a white solid.

WORKING EXAMPLE XXX

Preparation of 3-Hexyl-4-methyl-2,5-dihydrothiophene

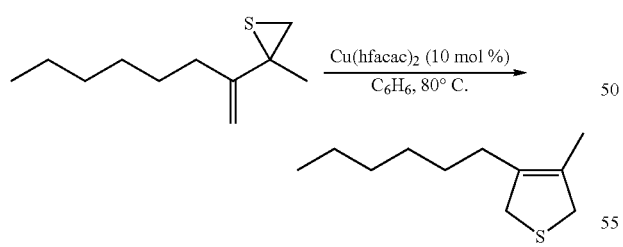

A solution of 1,2-epithio-3-hexyl-2-methyl-3-butene (40 mg, 0.22 mmol) and Cu(hfacac)$_2$ (11 mg, 22 µmol) in benzene (22 mL) were heated to 80° C. for 20 h under N$_2$. After cooling, concentration of the solvent in vacuo afforded a residue, which was purified by column chromatography (n-pentane) to give 3-HexylA-methyl-2,5-dihydrothiophene (30 mg, 75%) as a colorless oil.

WORKING EXAMPLE XXXI

Preparation of 4-methyl-2-pentyl-2,5-dihydrothiophene

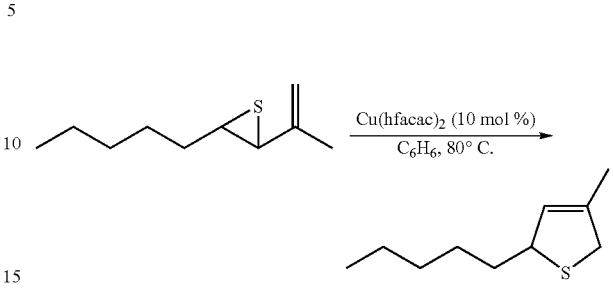

A solution of 2-methyl-3,4-epithio-1-nonene (50 mg, 0.29 mmol) and Cu(hfacac)$_2$ (14.5 mg, 29 µmol) in benzene (29 mL) was heated to 80° C. for 20 h under N$_2$. After cooling, concentration of the solvent in vacuo afforded a residue, which was purified by column chromatography (n-pentane) to give 4-Methyl-2-pentyl-2,5-dihydrothiophene (46 mg, 92%) as a colorless oil.

WORKING EXAMPLE XXXII

Preparation of 2,4,5,6,7,7a-Hexahydro-benzo[b]thiothene

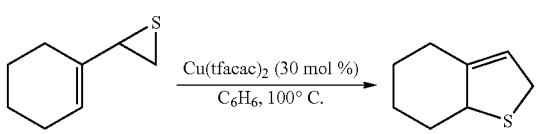 [SMILES: C1=C(C2CS2)CCCC1 ; C1=C2CCCCC2SC1]

A solution of 2-cyclohex-1-enyl-thiirane (100 mg, 0.7 mmol) and Cu(tfacac)$_2$ (78 mg, 0.21 mmol) in benzene (21 mL) were heated to 100° C. for 24 h under N$_2$. After cooling, concentration of the solvent in vacuo afforded a residue, which was purified by column chromatography (n-pentane) to give 2,4,5,6,7,7a-Hexahydro-benzo[b]thiothene (35 mg, 35%) as a yellow oil.

WORKING EXAMPLE XXXIII

Preparation of 2-hexyl-3-pentyl-2,5-dihydrothiophene

A solution of 1,2-epithio-3-pentyl-3-decene (20 mg, 83 ☐mol) and Cu(hfacac)$_2$ (4.1 mg, 8.3 µmol) in benzene (8.3 mL) was heated to 80° C. for 4.5 h under N$_2$. After cooling, concentration of the solvent in vacuo afforded a residue,

WORKING EXAMPLE XXXIV

Preparation of Ethyl 5-(2,5-dihydrothiophen-2-yl)pentanoate

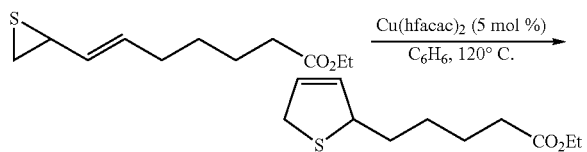

A solution of thiirane (E)-ethyl 7-(thiiran-2-yl)hept-6-enoate (40 mg, 0.19 mmol) and Cu(hfacac)$_2$ (4.7 mg, 10 μmol) in benzene (20 mL) was heated at 120° C. for 1.5 h in a pressure tube. Concentration of the solvent in vacuo afforded a residue, which was purified by column chromatography (n-pentane) to give Ethyl 5-(2,5-dihydrothiophen-2-yl)pentanoate (32 mg, 80%) as a colorless oil.

WORKING EXAMPLE XXXV

Preparation of N-Trityl-2,4,5,6,7,7a-hexahydrothieno[3,2-c]pyridine

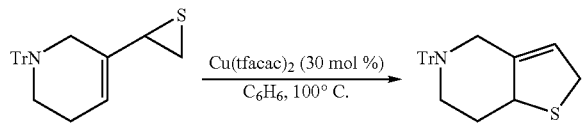

A solution of N-trityl-2,4,5,6,7,7a-hexahydrothieno[3,2-c]pyridine (38 mg, 0.99 mmol) and Cu(tfacac)$_2$ (11 mg, 30 μmol) was heated to 100° C. for 24 h under N$_2$. After cooling, concentration of the solvent in vacuo afforded a residue, which was purified by preparative TLC (hexanes:ethyl acetate, 100:1) to give N-Trityl-2,4,5,6,7,7a-hexahydrothieno[3,2-c]pyridine (20 mg, 52%) as a white solid.

VARIATIONS

The foregoing description of the invention has been presented describing certain operable and preferred embodiments. It is not intended that the invention should be so limited since variations and modifications thereof will be obvious to those skilled in the art, all of which are within the spirit and scope of the invention.

What is claimed is:
1. A method for preparing a compound having the structure

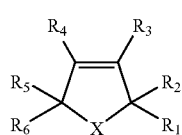
(A)

comprising the step of effecting rearrangement of

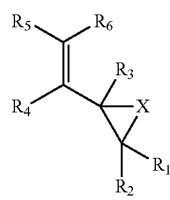
(B)

using a catalyst selected from the group consisting of

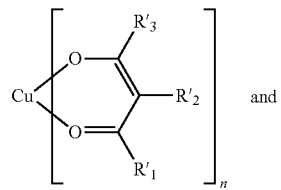
(III)

and

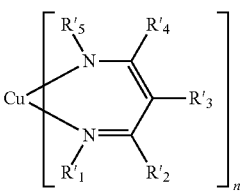
(IV)

and mixtures thereof, where R'$_1$, R'$_2$, R'$_3$, R'$_4$ and R'$_5$ are the same or different and are independently selected from the group consisting of hydrogen; C$_1$-C$_8$ alkyl which is unsubstituted or substituted with one or more of halogen or C$_6$-C$_{20}$ aryl; trifluoromethyl; and phenyl which is unsubstituted or substituted at the 4-position with fluoro, trifluoromethyl, C$_1$-C$_8$ alkyl or C$_6$-C$_{20}$ aryl; and n is 2, where X is selected from the group consisting of O, S and NR where R is a protecting group or other group that accommodates for N having a valence of 3, and where R$_1$, R$_2$, R$_3$, R$_4$, R$_5$ and R$_6$ are the same or different and are independently selected from the group consisting of hydrogen, C$_1$-C$_8$ alkyl, carbocyclic aryl group having 6 to 10 carbon atoms, heterocyclic aryl group having 6 to 10 carbon atoms, and halogen, and two or more of R$_1$, R$_2$, R$_3$, R$_4$, R$_5$ and R$_6$ can be bonded together to form a ring or rings.

2. The method of claim 1 where X is O.

3. The method of claim 1 where the catalyst has the structure (III) where R$_1$ and R$_3$ are CF$_3$ and R$_2$ is H and n=2.

4. The method of claim 1 where the catalyst has the structure (III) where R$_1$ is CH$_3$, R$_2$ is H, and R$_3$ is CF$_3$ and n=2.

5. The method of claim 1 where the catalyst has the structure (III) where R$_1$ and R$_3$ are CH$_3$ and R$_2$ is H and n=2.

6. The method of claim 1 where the catalyst has the structure (III) where R$_1$ and R$_3$ are 4-trifluoromethylphenyl, and R$_2$ is H and n=2.

7. The method of claim 1 where the catalyst has the structure (III) where R$_1$ and R$_3$ are 4-fluorophenyl and R$_2$ is H and n=2.

8. The method of claim 1 where the catalyst has the structure (III) where R$_1$ and R$_2$ are phenyl and R$_2$ is H and n=2.

9. The method of claim 1 or claim 3 where (B) is a vinyl oxirane having the structural formula

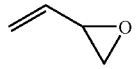

and (A) is a 2,5-dihydrofuran having the structural formula

10. The method of claim 1 where (B) is a vinyl oxirane having the structural formula

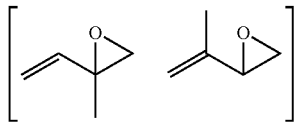

and (A) is a 2,5-dihydrofuran having the structural formula

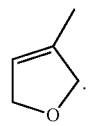

11. The method of claim 1 where (B) is a vinyl oxirane having the structural formula

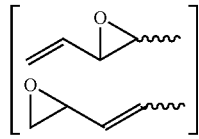

and (A) is a 2,5-dihydrofuran having the structural formula

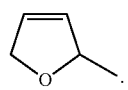

12. The method of claim 1 where the rearrangement is carried out at a temperature ranging from 50 to 300° C.

13. The method of claim 1 where the catalyst loading ranges from 0.01 mol % to 20 mol %.

14. The method of claim 1 where the reaction is carried out in a solvent which dissolves the vinyl oxirane and the catalyst.

15. The method of claim 1 where the reaction is carried out neat.

16. The method of claim 1 where X is S.

17. The method of claim 1 where X is NR.

18. A method for preparing a 2,5-dihydrofuran, comprising the step of rearranging a vinyl oxirane into a 2,5-dihydrofuran using a catalyst selected from the group consisting of

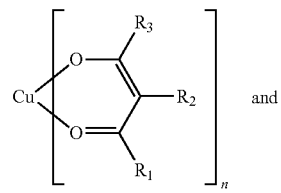

and

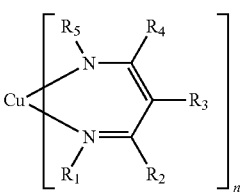

and mixtures thereof, where $R_1$, $R_2$, $R_3$, $R_4$ and $R_5$ are the same or different and are independently selected from the group consisting of hydrogen; $C_1$-$C_8$ alkyl which is unsubstituted or substituted with one or more of halogen or $C_6$-$C_{20}$ aryl; trifluoromethyl; and phenyl which is unsubstituted or substituted at the 4-position with fluoro, trifluoromethyl, $C_1$-$C_8$ alkyl or $C_6$-$C_{20}$ aryl; and n is 2.

19. The method of claim 1 where X is selected from the group consisting of O, S, NR and the catalyst is

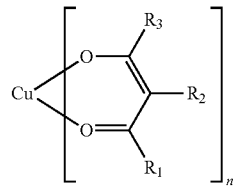

where $R_1$ and $R_3$ are $CF_3$, $R_2$ is H and n=2.

20. The method of claim 1 where the catalyst has the structure (III) where $R'_1$ and $R'_3$ are $CF_3$ and $R'_2$ is H.

21. The method of claim 1 where the catalyst has the structure (III) where $R'_1$ is $CH_3$, $R'_2$ is H, and $R'_3$ is $CF_3$.

22. The method of claim 1 where the catalyst has the structure (III) where $R'_1$ and $R'_3$ are $CH_3$ and $R'_2$ is H.

23. The method of claim 1 where the catalyst has the structure (III) where $R'_1$ and $R'_3$ are 4-trifluoromethylphenyl, and $R'_2$ is H.

24. The method of claim 1 where the catalyst has the structure (III) where $R'_1$ and $R'_3$ are 4-fluorophenyl and $R'_2$ is H.

25. The method of claim 1 where the catalyst has the structure (III) where $R'_1$ and $R'_2$ are phenyl and $R'_2$ is H.

26. A method for preparing a compound having the structure

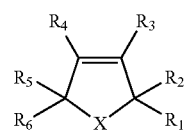

comprising the step of effecting rearrangement of

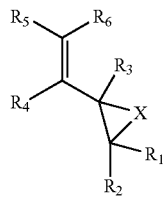

(B)

using an organic copper (II) activator, where the organic copper (II) activator is Cu(II) complexed with a ligand containing 1,3-carbonyl moiety, and where X is selected from the group consisting of O, S and NR where R is a protecting group or other group that accommodates for N having a valence of 3, and where $R_1$, $R_2$, $R_3$, $R_4$, $R_5$ and $R_6$ are the same or different and are independently selected from the group consisting of hydrogen, $C_1$-$C_8$ alkyl, carbocyclic aryl group having 6 to 10 carbon atoms, heterocyclic aryl group having 6 to 10 carbon atoms, and halogen, and two or more of $R_1$, $R_2$, $R_3$, $R_4$, $R_5$ and $R_6$ can be bonded together to form a ring or rings.

27. The method of claim 26, wherein the compound is a 2,5-dihydrofuran, comprising the step of rearranging a vinyl oxirane into a 2,5-dihydrofuran.

* * * * *